United States Patent [19]

Vaillancourt

[11] Patent Number: 4,511,359
[45] Date of Patent: Apr. 16, 1985

[54] STERILE CONNECTION DEVICE

[75] Inventor: Vincent L. Vaillancourt, Livingston, N.J.

[73] Assignee: Manresa, Inc., Hillsdale, N.J.

[21] Appl. No.: 426,260

[22] Filed: Sep. 29, 1982

[51] Int. Cl.$^3$ ............................................. A61M 5/00
[52] U.S. Cl. ..................................... 604/411; 285/3; 604/905
[58] Field of Search ................... 604/283, 905, 87, 88, 604/200, 201, 244, 411; 285/3

[56] References Cited

U.S. PATENT DOCUMENTS

| | | | |
|---|---|---|---|
| 3,986,508 | 10/1976 | Barrington | 604/905 |
| 4,256,106 | 3/1981 | Shoor | 604/905 |
| 4,433,973 | 2/1984 | Kurtz et al. | 604/905 |

Primary Examiner—C. Fred Rosenbaum
Assistant Examiner—Michelle N. Lester
Attorney, Agent, or Firm—Ralph R. Roberts

[57] ABSTRACT

This invention shows a sterile connection device as made in several embodiments but with a common purpose in which a protector may be pierced, penetrated or opened by pressurized fluid flow by means carried on a influent connector member but with the withdrawal of this means the protector is closed to the passage of unwanted contaminents. The influent connector may be conduit, a syringe or a like member with or without a needle, or a influent connector made as a molding and with or without a needle. The protector, if resilient, may be a secured diaphragm; a duckbill valve, or a slit in a resilient wall of a tubular member removably mountable on an extending tubular end of a effluent connector. The influent connector and the effluent connector are formed of plastic with molding processes providing the desired tolerances. The influent connector has means for conducting fluid to and through a small aperture therein and with this small aperture being in and through a small rigid structure device carried by the influent connector. A protector member of a resilient composition and characterized as having residual bias is adapted to be penetrated at a selected area by this small rigid structure carried by this half. A effluent connector has a fluid pathway and conduit therefrom. This effluent connector is adapted to receive and releasably retain this influent connector device and the protector member and with separation of the halves of the connection device the protector is carried in and remains within the effluent member so as to provide a barrier to unwanted contamination of the discharge conduit. A rigid protector is also shown with a one-way valve construction opened with pressurized fluid.

3 Claims, 24 Drawing Figures

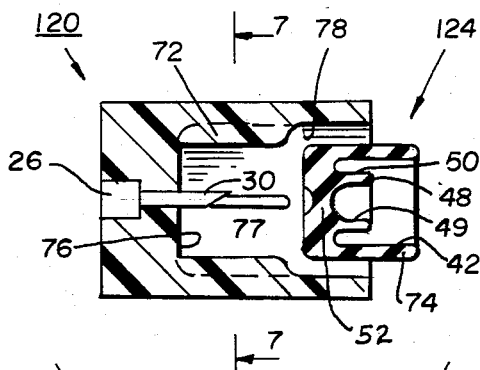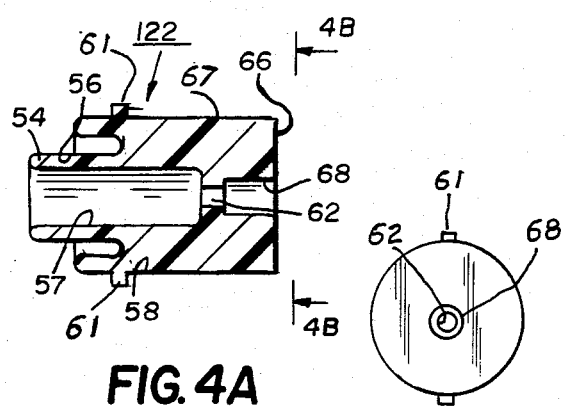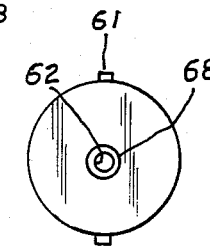
FIG. 5  FIG. 4A  FIG. 4B
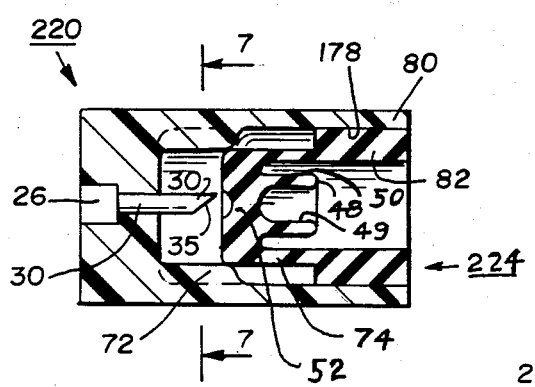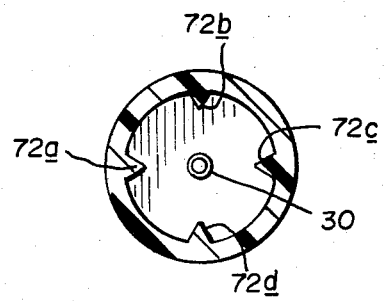
FIG. 6A  FIG. 7
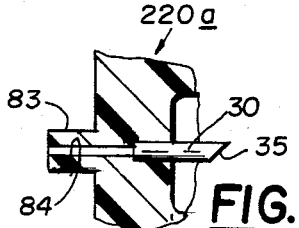
FIG. 6B
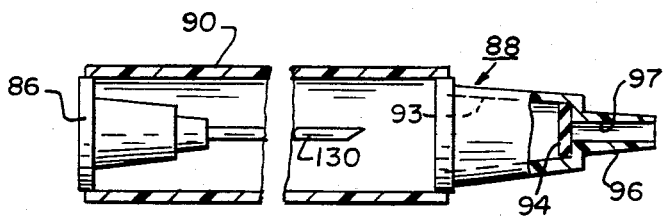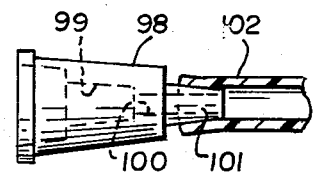
FIG. 8A  FIG. 8B  FIG. 8C

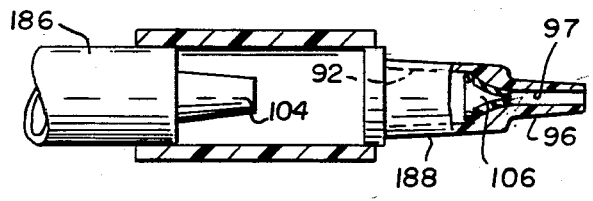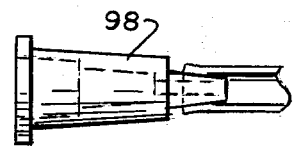
FIG 9A
FIG. 9B
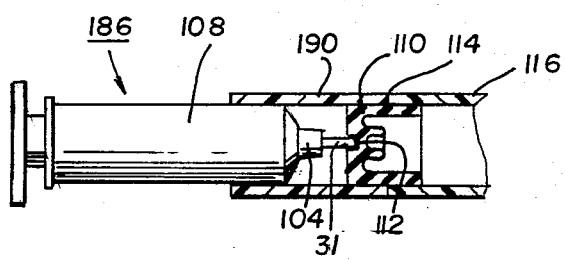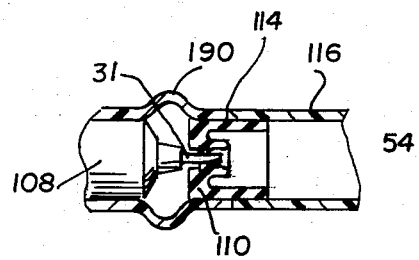
FIG. 10A
FIG. 10B
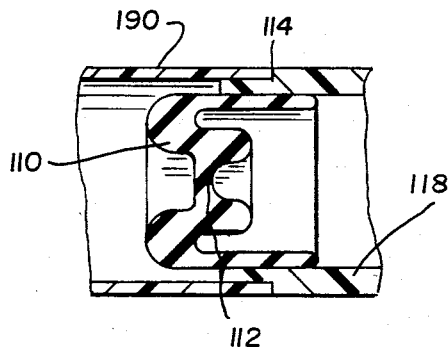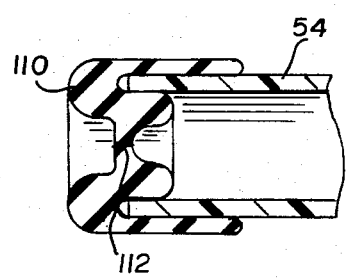
FIG. 10C
FIG. 10D

4,511,359

STERILE CONNECTION DEVICE

BACKGROUND OF THE INVENTION

1. Field of the Invention

This connector device is not specifically in a particular class and subclass since it is not only a valve but provides a protector member for both connector halves. Connectors are found in Class 251 (Valves and Valve Actuation); in Class 128 (Surgery); in Class 137 (Fluid Handling) and Class 222 (Dispensing).

2. Description of the Prior Art

Connectors for medical uses are well known and sterility for the patient is very important. Infection can and does undo the benefits of convenience "hook-ups" to a patient. Many attempts and concepts have resulted in both U.S. and Foreign patents. Recent peritoneal dialysis using connecting devices has focused attention on the problem of safe, effective and easily used sterile connector devices.

U.S. Pat. No. 4,294,250 to DENNEHEY as issued Oct. 13, 1981 shows a luer lock connecting device but exposure of a connector surface is possible and this device does not provide a positive exclusion. Also of note are U.S. Pat. No. 3,838,843 as issued to BERNHARD on Oct. 1, 1974 which shows a rubber tube but no transfer; U.S. Pat. No. 3,986,508 to BARRINGTON as issued Oct. 19, 1976 and uses two rubber inserts each of which remain in their "as-placed" condition and position. Removal and transference of the resilient member is not shown or suggested in this apparatus, and U.S. Pat. No. 4,004,586 to CHRISTENSEN et al as issued Jan. 25, 1977 shows a connecting device but no automatic transfer.

Also know are U.S. Pat. No. 4,143,853 to ABRAMSON as issued Mar. 13, 1979 which contemplates a rubber valve means; U.S. Pat. No. 4,187,846 to LOLACHI et al as issued Feb. 12, 1980 which shows a connecting device but employs a movable shield plate; U.S. Pat. No. 4,201,208 to CAMBIO, Jr. as issued May 6, 1980 employs a rubber wall that is pierced but no transfer is contemplated; U.S. Pat. No. 4,203,443 to GENESE as issued May 20, 1980 shows a connecting device but no transfer member insuring sterility; U.S. Pat. No. 4,209,013 to ALEXANDER et al as issued June 24, 1980 shows a connecting device but no transfer member; U.S. Pat. No. 4,215,690 to OREOPOULOS et al as issued on Aug. 5, 1980 shows a needle without a transfer member, and U.S. Pat. No. 4,310,017 to RAINES as issued Jan. 12, 1982 shows a Y-block connector.

Foreign patents are noted as follows: British Pat. No. 1,199,498 as published July 22, 1970 shows a rubber cap used in a syringe device and the Austrian Pat. No. 29 22 940 as issued Dec. 13, 1979 to Imed Corp., San Diego, Calif. which shows a rubber cap which acts as a one-way valve, but transfer of this cap is not contemplated with and by use of this apparatus.

Coupling devices are well known and are particular to the field of use. Electrical connectors are widely used as are the connectors for fluid flow. The connector device of this invention is particularly used and useful for fluid flow in the field of medicine when and where sterility is to be maintained at the time of disconnect. Kidney deficiency or failure has led to the use of dialysis which requires repeated "hook-up" to the blood system or to the recently adopted continuous ambulatory peritoneal dialysis. CAPD "Continuous Ambulatory Peritoneal Dialysis" has been developed by the medical community and costs about one-half that of conventional dialysis. This CAPD is less traumatic to the body of the user, requires far less time and more importantly can be done at home. User these circumstances a sterile connecting device is especially important.

It is estimated that about fifty thousand people need dialysis treatment to live. CAPD uses a small, flexible catheter surgically implanted into the patient's abdominal cavity. A plastic bag containing the treating solution is attached to the catheter and through gravity this solution is fed through the catheter and into the bottom of said abdominal cavity. The emptied bag, although still attached, is now clamped and stored in the patient's pocket. The waste products in the blood are drawn by natural means into the solution. The impurity laden fluid is then drained from the cavity into the bag which has now been placed on the floor. Although as many as four bags per day may be needed for cleansing the blood of a patient, the patient need but only half an hour to make each complete exchange and at the other times the patient is unemcumbered. This exchange process is painless and the patient quickly becomes accustomed to the pressure of the dialysis fluid in the abdomen and in the use of this system.

A problem with this method and others using implanted catheters is the contamination developed by handling. It is essential that a sterile connector half as provided by the several embodiments of this invention insure that the catheter end be protected at the time of disconnection of the device. Use of a new connector requires the removal and discarding of the movable and transferred protector member and the use of a new connector half and a new protector member. This assembly provides such an assembly with sterility maintained at disassembly.

SUMMARY OF THE INVENTION

This invention may be summarized, at least in part, with reference to its objects. It is an object of this invention to provide, and it does provide, a connector assembly device that insures sterility before, during and after use. This assembly includes male and female halves in which a movable resilient protector member is retained and is penetrated at the time of fluid transfer through this connector assembly and a connected tubing member. The male connector half of this assembly has means for engaging and retaining this protector member which, when the female half is withdrawn from the assemby, provies exclusion of particles to the conducting passageway and also to the contacting surface of the male half.

It is a further object of this invention to provide, and it does provide, a sterile connector assembly device which includes male and female halves and a protector member with said protector having an outer diameter portion which is slidably retained by a plurality of flutes provided in a bore portion formed in the female half. These flutes provide the required friction fit sufficient to retain the protector member and release same to the female connector once a connection has been effected. Friction fit of the protector to the male connector portion is greater than the friction fit and resistance of the protector when positioned in the female connector. These flutes also provide an air escape means at the time when the connector is brought together as an assembly.

This air escape path enables a needle carried in and by the female half to puncture and penetrate a transverse wall of the protector without causing a pressure to develop as and when fluid transfer is made to an attached tubing.

It is a further object of this invention to provide, and it does provide, a sterile connector assembly device which includes a syringe and a tubular sheath which provides a guide movement of the syringe toward and to the connector assemby. This assembly includes a connector half having a recess in which the inner end portion is closed with a fixedly secured diaphragm of resilient material. This syringe includes means for penetration of the diaphragm sufficiently to enable the fluid in the syringe to be expelled therefrom to and past the diaphragm and into a receiver and a connected tubing.

It is a still further object of this invention to provide, and it does provide, a sterile connector assembly device in which the connector member is molded of substantially rigid plastic and resilient means is provided so that applied pressure causes a "one-way" valve means in this connector to be opened for the passage of pressurized fluid. This valve closes at the cessation of the pressure. This protector has means for retention of the protector on the discharge half of the connector as and after disassemby of the device. Retaining the connector halves as an assembled unit during fluid transfer is by exemplified means and the like.

In brief, the following description pertains to a connector assembly for fluids including gasses in which the connector assembly is sterilized and said sterility is maintained during and after mounting to a tubing conductor. In the several embodiments a protector member has an initially inviolate transverse wall that is penetrated, pierced or otherwise opened for transfer of fluid into a receiver and connected tubing. Disassembly of the connector or removal of one of the connector portions of the assembly allows the protector member to close so as to exclude particles and bacteria from the passageway and the interior of the conductor tubing.

Several embodiments are shown and described in detail in the specification and claims but it is to be noted that each embodiment has a protector member having a segment initially opened for fluid transfer and at the disconnection of the assembly or a loss of fluid pressure this connector segment is caused to close and exclude contaminants from the connected tubing passageway. The connector assembly is mainly directed to and toward medical use in which sterility is to be maintained. A female and male connector has a contoured tubular protector member which is retained on an extending tubular portion of the male connector half. This protector remains on the pertinent connector surfaces of the male connector half during disassembly and use and until time to be reconnected to a new connector half. A needle may be carried in the female half and is disposed to puncture the transverse wall in the protector. Flutes are provided in the female connector in an alternate embodiment and provide guide means and alignment for the protector in the female half.

Still further alternate connector assemblies anticipate the use of a fixed conduit member which may be syringe means with and without attached needles. The use of a syringe or fixed conduit to carry a fluid to be transferred to a tubing conduit anticipates a sheath portion. This sheath is of tubular configuration and is sized to be retained on the syringe barrel or fixed conduit member and is slidable thereon. The sheath may be rigid, semi-rigid or flexible. The protector may have a wall for piercing by an attached needle or when the syringe is used without a needle, the protector may have a closed slit or aperture.

The protector member is usually resilient but may be made of substantially rigid plastic providing means for retention on the discharge half of the connector and means for initial retention in and on the other half of the connector. The protector member has a one-way valve or a small resilient portion that allows the protector to provide an inviolate retainer portion when and during disassembly and until a new connection is to be made.

In the drawings the connector assembly is shown with a female and male portion and although fluid is caused to flow in both directions the initial supply is usually from a bag or container, and for the purpose of easily identified connector portions the female half is identified as the influent portion and the male half is identified as the effluent portion. The protector member is carried within the influent half and at and after fluid transfer and disassembly of the connector device remains on the effluent half as a protector of the conduit and critical surfaces of the effluent portion.

In addition to the above summary the following disclosure is detailed to insure adequacy and aid in understanding of the invention. This disclosure, however, is not intended to cover each new inventive concept no matter how it may later be disguised by variations in form or additions of further improvements. For this reason there has been chosen specific embodiments of sterile connector assemblies as adopted for use for transferring fluids and showing a preferred means for constructing and using these connector assemblies. These specific embodiments have been chosen for the purposes of illustration and description as shown in the accompanying drawings wherein:

BRIEF DESCRIPTION OF THE DRAWINGS

FIG. 1 B represents a fragmentary side sectional view and showing the needle as an integrally molded portion of the female connector and showing the protector with a shortened fore or front portion to mate with the shortened integral needle;

FIG. 4 A represents a side sectional view of an alternate construction of a receiving male connector half;

FIG. 4 B represents an end view of the receiving male connector half of FIG. 4 A and showing pin protrusions that provide a bayonet lock, this view taken on the line 4 B—4 B and looking in the direction of the arrows;

FIG. 5 represents a side sectional view of a female connector half similar to that of FIG. 2 and with the molded connector having fluted ribs which provide guide and retention means for the resilient protector member;

FIGS. 6 A and 6 B represent side sectional views of yet another female connector half quite similar to the connector half of FIG. 5 but with an outer guide tubular member extended to provide a guide for an enlarged and extending skirt portion of a resilient protector member;

FIG. 7 represents a sectional view taken on the line 7—7 of FIGS. 5 and 6 A and looking in the direction of the arrows;

FIGS. 8 A, 8 B and 8 C represent sectional side views, partly diagrammatic, of a sterile connector assembly in which a conventional syringe with attached needle is provided with a connector and receiver;

FIGS. 9 A and 9 B represent sectional side views, partly diagrammatic, of a syringe without a needle and with a connector and receiver;

FIGS. 10 A, 10 B, 10 C and 10 D represent side sectional views of an alternate resilient protector device used with a syringe or rigid conductor member, this protector device having a slit at its midportion which is sufficient and adapted to allow a needle portion of a syringe or rigid hub conductor to pass through this slit and to be in flow communication with the effluent conduit;

FIG. 11 B represents a sectional view, partly diagrammatic, and showing the construction of said one-way valve in the protector member, this view taken on the line 11 B—11 B of FIG. 11 A and looking in the direction of the arrows, and FIGS. 12 A, 12 B and 12 C represent alternate connector retaining means exemplifying apparatus and construction for retention of the two halves of the assembly.

In the following description and in the claims various details are identified by specific names for convenience. These names are intended to be generic in their application. Corresponding reference characters refer to like members throughout the several figures of the drawings.

EMBODIMENT OF FIGS. 1 A, B, 2 AND 3

Referring next to the drawings and in particular to the embodiment shown, there is illustrated a sterile connector assembly in which three components or members are needed to provide the inexpensive and substantially fool-proof connector means. A female connector half 20 is preferably molded of relatively stiff plastic which is acceptable for medical or like purposes. A male connector half 22 is sized and adapted to mate with the female connector half 20. A protector portion identified as 24 is shown in section as plastic or rubber. As a practical matter, this portion is made of rubber or a resilient rubber-like material and is carried in the bore of the half 20 and ahead of half 22.

Figure 2:
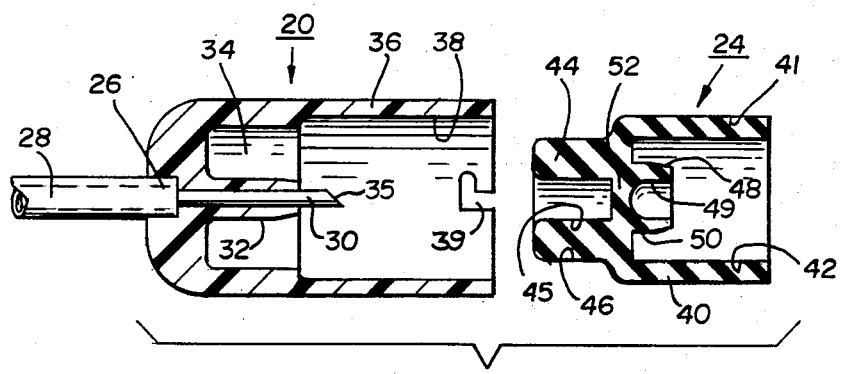
FIG. 2 represents a side sectional view of the female connector half and the flexible cover and protector member of FIG. 1 in an "as-formed" condition.

As seen in FIG. 2, the female connector half 20 which is the (influent) delivery half has a receiving recess 26 in which is fixedly secured a length of flexible tubing 28. A needle 30 which is of metal tubing is also fixedly secured and carried by support post portion 32 that extends forwardly in tubular recess 34. It is to be noted that the extending end of needle 30 is sharpened such as by a bevel angle 35 and protrudes a determined amount from the end of support post portion 32. A skirt portion 36 surrounds an internal circular cavity 38 of a determined size and extent. At the right end of this skirt there is shown a L-shaped cutout or receiver 39 which is conventional in bayonet locks for securing of two components together to prevent accidental and/or unwanted disengagement of the secured components.

The protector member 24 is molded of a resilient material which also meets government agency approval for medical and like uses. The protector member 24 is formed with a larger outer tubular skirt portion 40 having an outer diameter 41 slidable in cavity 38 of connector half 20. An internal diameter 42 is sized to provide a friction fit over and on a tubular extending portion of the male connector half 22. A forward end portion 44 has an inner diameter recess 45 which has a slight interference fit on the post portion 32 of the female connector 20. An outer diameter 46 is a clearance fit in the tubular recess 34. This protector member 24 (FIG. 2) is also formed with a tubular inner member 48 having inner and outer diameter portions 49 and 50. An initially impervious wall portion 52 is formed and positioned between the inward end of the recess formed by the inner diameter portion 45 and inner diameter portion 49.

ALTERNATE CONNECTOR AS IN FIG. 1 B

Figure 1A:
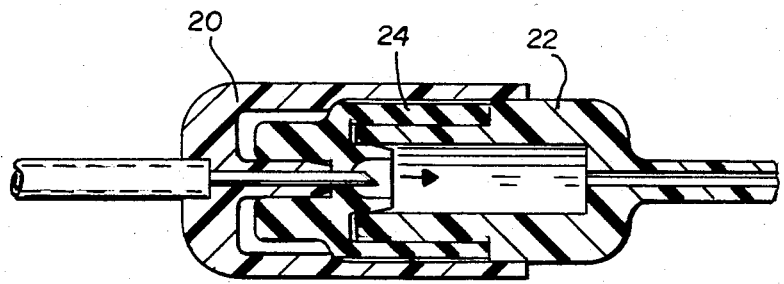
FIG. 1 A represents a side sectional view of an assembled sterile connector of this invention, this view partly diagrammatic and showing the relative position of the three components at time of fluid flow.
Figure 1B:
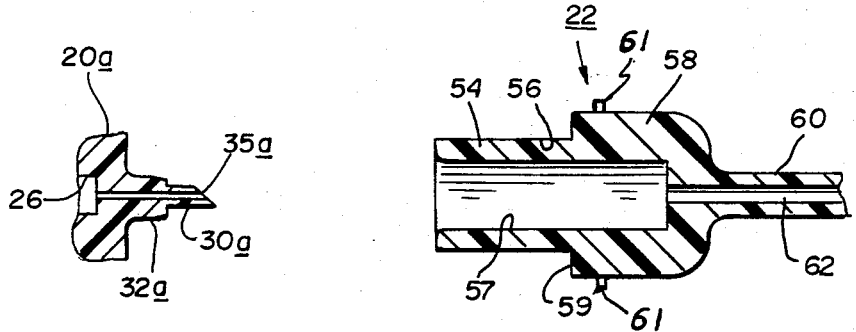

Referring next to FIG. 1 B, the influent connector 20 a, rather than using a metal needle as in FIG. 1 A, may be molded as an integral needle 30 a with a conduit 53 formed therethrough. The projecting portion of the needle is adapted to penetrate through the tranverse wall portion 52 of the protector 24. The forward end portion 44 of the protector 24 is made of a length to suit the penetrating length of the needle portion 30 a and with the forward end portion 44 and the cavity 45 also sized as to diameter and length to suit the interior configuration of the connector 20 a.

Figure 12A:
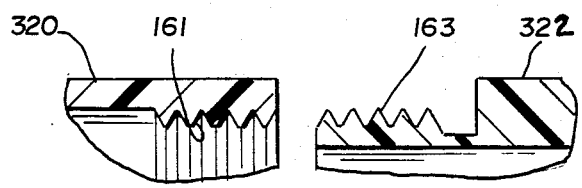
Figure 12B:
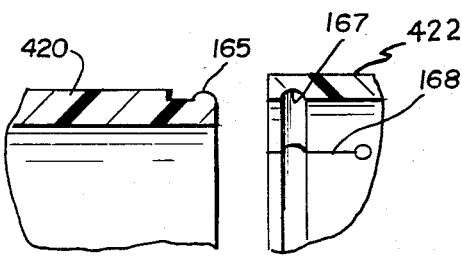
Figure 12C:
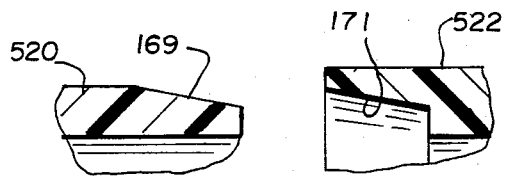

The male connector half generally identified as 22 (FIG. 3) is also molded of a rigid or semirigid plastic that is of a material acceptable for intended use. This molding includes a forward tubular extending portion 54 having outer and inner diameter portions 56 and 57. The outer diameter portion is terminated at a greater diameter portion 58 forming a shoulder 59. This larger diameter portion terminates as a reduced diameter connector extension 60. Pins 61 are depicted in this view and are used with bayonet cutout 39 in skirt 36 as seen in FIG. 2 to effect a bayonet lock securing means. In FIGS. 12 A, B and C are depicted other securing means. A fluid passageway 62 extends from the internal portion 57 to and through the hub and connector extension 60 of this half portion.

USE AND OPERATION OF EMBODIMENT OF FIGS. 1 A, 1 B, 2 and 3

The inlet connector (female) and protector 24, as an assembly, are sterilized by conventional and approved means and usually are stored and shipped in a sterile protective package (not shown) containing in addition tubing, bag, etc. The influent connector half portion 20 is the connector member portion to be discarded after use. The tubing member 28, which is connected to the influent or female half 20 and needle 30, has its inner end adjacent to but not in a penetrating position to and through wall 52. The male half 22, which is separately provided and initially carries the protector member, is positioned so that the forward tubular extension 54 is seated in the tublar recess of the protector member 24. This recess is disposed between diameter 42 and diameter 50. The connector extension 60 is connected to or is a part of male connector half 22 and is usually secured to and through the skin of the patient. In use, the protector 24 is positioned so that neither outer surface 56 and inner surface 57 is touched while protector 24 is pulled off the tubular portion 54 of the male (effluent) connector 22.

Female (influent) connector 20, containing the protector 24 within its cavity, is attached to the male (effluent) connector 22. During attachment, due to the design of the female connector inner cavity, the protector 24 mechanically engages and is forced on and over the surface 56 of the tubular portion 54 of the connector 22. Concurrently, the needle 30 or 30 a pierces the transverse wall portion 52 of the protector 24. A slight twisting movement secures the two connector portions with the bayonet lock or fitting. The pins 61 enter and are engaged and retained by the L-shaped cutouts 39 in the skirt 36. In this manner a protector is specifically positioned on the male connector 22 and concurrently is established in a sterile condition, a pathway through the protector for fluid using the needle 30 or 30 a on the connector 20. Fluid flow through needle 30 and to the passageway 62 is established and when and where reverse flow is to be made this connection assembly is maintained. If desired a gravity or shut-off (not shown) may be employed to control the fluid flow.

This piercing of the wall 52 by the sharpened end 35 of the needle 30 occurs when flow communication is to be achieved. A forward push, twist or other manipulation brings the connector halves 20 and 22 to the position of FIG. 1. Flow of fluid and/or the like is as indicated by the arrow. When a reverse flow is to be made as in the case of CAPD from the patient to the storage bag the flow is counter to the indicated arrow. When and where a disconnect is to be achieved, the female half 20 is removed whereat the needle is withdrawn from the protector member 24 and the wall portion 52, although punctured, closes to provide a self-seal. The resilient protector member 24 remains on the extending tubular portion 54. Of particular note is that the tubular skirt 40 provides a protective barrier to the exterior surface 56 of the male connector.

The protector remains on the connector 22 until a new hook-up is to be made whereat by manipulation the protector 24 is manually removed from the surface 56 and the interior remaining aseptically clean while a reconnection is achieved. A female coupling half 20 with a new protector 24 therein is placed on the male coupling half 22 and replaces the original or previously removed and discarded protector 24. It is to be noted that the protector 24 insures sealing of the male connector 22 during the disconnect period but also prevents contamination of the surface 56 and the interior of the male connector half 22 when and while separation occurs. There is a slide fit of the resilient protector as to outer diameter 41 in cavity 38 and a surface 56 is an interference fit with the internal diameter 42 of the protector.

It is to be noted that initial assembly of the connector contemplates that male connector half 22 and protector 24 will be assembled before placement into the body cavity. Another female connector 20 containing another protector is now prepared. The protector on the effluent half 22 is now removed and the influent connector is now attached to effect the assembly of FIG. 1 A. Connector half 20 is attached to tubing, a bag or the like. Sterility is provided by conventional methods and at the time of use the assembly of FIG. 1 A may have the sharpened end 35 of the needle 30 pushed through the wall 52 to establish a fluid flow pathway. The wall 52 may have a cut which enables advancement of the needle 30 with less resistance. With or without a cut, the wall 52 closes after the withdrawal of the needle 30 so as to exclude bacteria and other contaminents from entering the inner end of the forward extending portion 54 of the male connector 22. The protector 24 also protects surface 56 until removal of the resilient member 24. Member 24 is contemplated to be a molding with precise sizes and may be resilient and when so molded is of a rubber or rubber-like material.

EMBODIMENT OF FIGS. 4 A and 4 B

Figure 3:
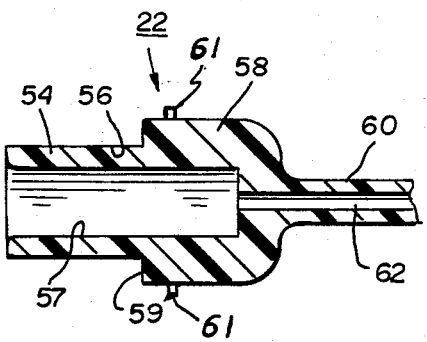
FIG. 3 represents a side sectional view of the receiving male half connector of and for the assembly of FIG. 1.

This connector portion as shown in FIGS. 4 A and 4 B and identified as 122 is contemplated to be assembled by bayonet means. The L-shaped cutout 39 in the skirt of the mating connector utilizes the pins 61 seen in FIG. 4 B and assembly contemplates a twisting motion usually associated with such a lock retention. This male (effluent) half connector 122 also is shown with a circular recess 68 into which a catheter, not shown, may be mounted. In all other respects the extending tubular end 54 with its outer and inner diameter portions 56 and 57 as in FIG. 3 is in flow communication with fluid passageway 62. This male connector member may be used with the components of FIG. 2 or with other alternate constructions to be further identified.

EMBODIMENT OF FIG. 5

In FIG. 5 a female connector half identified as 120 is adapted and sized to mate with and be used with the male receiver half 122 as seen in FIGS. 4 A and 4 B. The half (effluent) 122 is depicted with a rear face 66 which is substantially transverse but may be shaped to suit. The outer diameter 67 is a slide fit within the skirt of the mating coupling. An internal recess is formed in half 120 and with a plurality of flute or rib portions 72 which as seen in FIG. 7 are four in number and are identified as 72 a, b, c and d. These flutes, as depicted, are rather triangular in configuration but may be of a narrow key configuration or rounded. The shape of these flutes are merely a matter of design as long as the inner retaining surfaces are sufficient to support and retain a resilient protector generally identified as 124. These flutes 72 engage the outer diameter surface 74 of this protector. These flutes are of sufficient length and size so as to provide a friction fit between the outer diameter of the protector 124 and the inner surfaces or edge of the flutes. These flutes also provide for the expulsion or flow of any air trapped between the inner face 76 of the cavity 70 and the forward face 77 of the protector 124 when and as the protector is expanded by the penetrating action of the needle 30 or 30 a. The female half 120, at the termination of the flutes 72, has a smooth circular inner surface portion 78. This tubular surface portion is a slide fit with diameter 58 provided on member 22 or 122. The protector 124 is also contoured or formed at its inner extent with a tubular inner member 48 having the inner and outer diameter portions 49 and 50. The skirt portion of this connector half has a retaining means such as the L-shaped cutout 39 shown in FIG. 2 and pins 61 are provided on the mating portion.

USE AND OPERATION OF EMBODIMENTS OF FIGS. 4 A, 4 B AND 5

In the manner of FIGS. 1 through 3, above described, the embodiments of FIGS. 4 A, 4 B and 5 are used. The protector 124 is mounted in the female connector half 120 with the forward end of the protector against the entering end of the needle 30. It is to be noted that the needle 30 is not carried by a support post 32 so this female connector half is shortened correspondingly. The protector 124 is mounted and is retained by the flutes 72 and the outer diameter of protector 124 with this protector positioned so that the retaining groove is seated on the tubular extending portion 54 of the male half 122. When it is desired to effect fluid flow and connection the needle 30 is pushed through the resilient central wall portion of the protector 124. The flutes 72 enable trapped air to exit along surface 78 and diameter 58 until faces 76 and 77 are brought together or substantially together. Separation of the halves has the protector 124 remaining on the extending tubular member 54 and protecting surface 56 until a new connector is to be used.

EMBODIMENT OF FIGS. 6 A AND 6 B

In FIGS. 6 A and 6 B the female connector of FIG. 5 is altered to provide an extended outer guide skirt. This female half is identified as 220 and includes secured needle 30 at the terminal end of and in flow communication with recess 26. Flutes 72 are provided in this molding but extending to the right of these flutes is the smooth inner portion or bore 178 of tubular skirt 80. This bore 178 is sized to slidably retain an outwardly tubular or skirt portion 82 of a resilient protector member 224. The protector member 224 has the tubular inner member 48 with inner and outer diameters 49 and 50 which provides the circular groove into which the extending tubular member of the male connector is seated. As seen in FIG. 6 A the tubular portion 82 and the bore 178 are disposed to terminate at or substantially at the same right end. At this position the smaller diameter 74 is seated in the flutes 72 but the needle 30 has not pierced the end wall 52. The extending tubular end of the male half portion either 22 or 122 is sized and of a length to suit the length of inner diametrical portion 49.

In FIG. 6 B the influent connector of FIG. 6 A has been altered to show that the molding identified as 220a is made with an extending tubular portion 83 and a passageway 84 extends therethrough. The needle 30 may be a metal member 30 or may be integrally formed as a molded member 30a. This is merely a matter of selection and preference.

EMBODIMENT OF FIGS. 8 A, 8 B AND 8 C

In this embodiment there is depicted an alternate connector assembly for use with a syringe with an attached needle. A syringe or similar rigid conductor device is identified as 86 and has a connector used therewith made of suitable rigid plastic and identified as 88. The needle used therewith is identified as 130 and may be fixedly secured to the discharge end of the syringe or mounted by having a tapered socket attached to a tapered end of the syringe in a conventional manner. The connector member 88 is maintained in alignment with the barrel portion of the syringe by a tubular sheath 90. This sheath 90 may be fixedly or slidably secured to either or both the syringe or the connector.

This connector 88 is preferably a molded member with a tapered socket 93 in which the small (right end) portion is fixedly mounted with a diaphragm 94. This diaphragm is made of resilient material that is easily pierced by the sharpened end of the needle 130. This connector at its right end is formed with a tapered hub 96 in which and through which a passageway 97 extends. As depicted, this assembly is also provided with a receiver formed as a molding 98 and having therein a tapered recess 99 which is a retaining fit with the tapered hub 96 of connector 88. A fluid passageway 100 extends from this recess 99 to the interior of an attached flexible tubing 102. In use, it is contemplated that the receiver 98 will be mounted to the connector 88 during the penetration of the diaphragm 94 by the needle 130 and the expelling of the contents of the syringe 96 in the reservoir 86 and then through the needle.

Separation of the connector 88 from the receiver 98 allows a new fluid reservoir 86 and connector 88 to be attached to receiver 98 for transferring the contents of this reservoir through the needle, diaphragm and into the tubing 102. It is to be noted that the interior of the connector 88 is protected by the tubular sheath 90 and passageway 97 by the diaphragm 94. The receiver 98 is mounted on the connector half 88 during the initial transfer of fluid from the syringe to the tubing 102. The connector 88 and receiver 98 remains in the removably joined together condition until new reservoir is to be used. The reservoir 86 and tubular sheath 90 may be used with a new connector half 88 in which condition the immediately preceding connector 88 is removed from receiver 98 and this new connector and reservoir are mounted.

EMBODIMENT OF FIGS. 9 A AND 9 B

In FIGS. 9 A and 9 B there is depicted an alternate construction in which, for convenience, a syringe 186 is provided with a tapered small end 104. A connector 188 has a tapered socket 92, a hub 96 and a passageway 97 as in FIG. 8 B above described. A duckbill valve 106 is carried and secured at the forward or inner end of the socket 92. This duckbill valve is adapted to be opened when and with the forward movement of the small end 104 of the syringe into the tapered socket 92 and fluid pressure is applied. The receiver 98 is similar to or identical to that above described in connection with FIG. 8 C above.

EMBODIMENT OF FIGS. 10 A, 10 B, 10 C AND 10 D

Referring to the embodiment of FIGS. 10 A, 10 B, 10 C and 10 D, there is shown, again for convenience, a syringe 186 as in FIG. 9 A but with a resilient and/or flexible tubular sheath identified as 190. This tubular sheath 190 is attached to a barrel portion 108 and has an outer surface adaptable for fixedly attaching said sheath 190 as by cement or the like. The discharge end of the syringe or similar rigid conductor is made with a small tapered end 104. A resilient protector 110 has a slit 112 therein and therethrough and provides the forward wall end portion of the protector. This protector is sized and adapted to be mounted and retained on the forward extending portion 54 of a male connector half 22 or 122 as seen in FIG. 3 or FIG. 4. Of particular note is cut or parting line 114 for a tubular portion 116 fixed to male half 122 or 22. The shoulder adjacent outer portion 56 on male half 22 or 122 may also be employed without the tubular portion 116.

In FIG. 10 C the protector 110 is shown with a tubular portion 118 within which the protector 110 is movable. The resilient tubular sheath 190 abuts against a shoulder portion of member 118 at parting line 114. This may be a separate tubular portion which engages the forward extending portion 54 or may be an integral portion of the connector member. It is important and necessary that the forward movement of the syringe 186 or similar rigid conductor bring the tapered end 104 or the extending lumen 31 into and through the slit 112 without movement of the protector 110 from its positioned mounting on the extending portion 54 or a like member. FIG. 10 D shows the protector 110 on an extending forward portion 54 as seen in FIG. 3.

USE AND OPERATION OF THE EMBODIMENT OF FIGS. 10 A, B, C AND D

In use this embodiment contemplates that the syringe 186 (rigid or semi-rigid conduit) retain the desired fluid as to amount and composition. The syringe or conduit 186 is manipulated to bring the tapered end 104 to and into the protector member 110 and the slit 112 therein. The tapered end 104 is moved sufficiently forward so that the syringe is in discharge condition. The resilient tubular sheath bulges or collapses sufficiently for the lumen 31 at the end of the discharge conduit to pass through the now open slit 112. The conduit in the tubular extending portion 54 carries the expelled fluid from the syringe or conduit 186 to the flexible tubing.

When and where a tubular portion 118 is provided it is contemplated that the resilient protector 110 is secured to and is retained by the forward extending portion member 54 after transfer of fluid and withdrawal of the syringe or conduit 186 and tubular sheath 190.

RIGID CONNECTOR OF FIGS. 11 A AND B

Figure 11A:
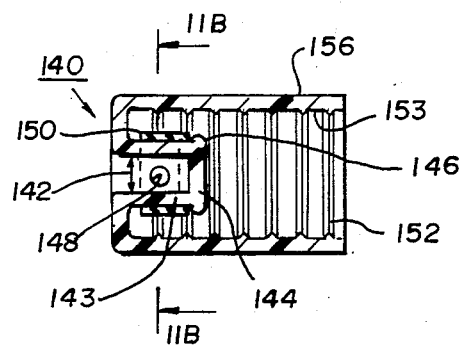
FIG. 11 A represents a sectional side view, partly diagrammatic, of a protector member molded of substantially rigid plastic and adapted for mounting in the influent half on the connector and at the completion of assembly having ribs that grip the extending tubular portion of the male connector sufficiently to effect the retention of the protector on said tubular portion.
Figure 11B:
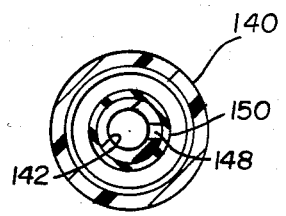

In FIGS. 11 A and 11 B there is depicted a protector as a molding and generally identified as 140. This protector is contemplated as being molded of polypropylene and is generally tubular with a transverse closed end. This transverse end portion is formed with a slightly tapered socket central portion 142 with wall 143 and terminating inwardly with a closed end portion 144. This end portion is formed with a slight projection or stop 146 thereon. A small access hole or passageway 148 is formed in the wall portion of central socket portion 142. A biased tubular band 150 which may be spring metal or plastic is a snug fit on the larger diameter of central portion 142 and provides a one-way valve action permitting fluid flow when the flow is to the central portion 142 and is pressurized, and closing when fluid is caused to flow from the effluent connector and towards the central portion 142. It is to be noted that a plurality of small ribs 152 are disposed on and extend from the inward surface 153 of the protector outer tubular member or skirt portion 156.

USE AND OPERATION OF THE PROTECTOR OF FIGS. 11 A AND 11 B

The protector 140 is contemplated to be used with an effluent connector as in FIGS. 3 and 4 and the ribs 152 are disposed to tightly engage the extending tubular portion 54. The tapered socket 142 is a fluid tight fit on a tapered end of a mating inlet connector. Such a tapered end and hub is found on syringes and the like. This protector is contemplated to be used with fluid delivered by and with a small amount of pressure. Pressure causes the fluid delivered ahead of and trapped by the hub, the tapered socket 142 and end 144 to flow to and through hole or aperture 148 and displace tubular band 150 so that this pressurized fluid flows through opening 148 and into the effluent connector. When and as pressure ceases, the resilient band 148 again seats on wall 143 to stop reverse flow of fluid to and through the hole 148 into the connected hub. The ribs 152 prevent removal of the protector 140 from an effluent connector portion except by manipulation by the operator.

EMBODIMENTS OF FIGS. 12 A, 12 B AND 12 C

Referring next and finally to FIGS. 12 A, 12 B and 12 C, there is illustrated alternate means for retaining the two connector halves in a together relationship during use. In FIG. 12 A influent connector 320 is depicted with threads 161 which engage and mate with threads 163 on effluent connector 322. In FIG. 12 B influent connector 420 is depicted with a ring 165 which is engaged by a snap retainer 167 formed on effluent connector 422. The ring 165 and retainer 167 may be reversed as to construction. The retainer portion 167 is formed with a plurality of longitudinal slots 168 enabling the retainer portion to be advanced over the retaining ring portion 165 when and as the connector halves are brought together in a joined relationship. In FIG. 12 C influent conductor 520 is shown with a retaining taper portion 169 which mates with and seats in a female tapered portion 171 formed on effluent connector 522. As in FIG. 12 B the male and female tapered portions may be reversed and formed on the mating connector half. Other connecting means for disconnectable retention may be provided but with the bayonet lock above exemplify well known retaining means.

It is to be noted that in the several embodiments above described the connector assembly anticipates a resilient protector interposed in one of the halves and retained in the position during withdrawal of the initial connecting member. In FIGS. 1 through 6 B it is anticipated that the protector member is initially placed in the female half portion and onto the projecting tubular end of the receiver. During the discarding of the female half the protector is in position to effect a closing and provide a tight-fitting shield to insure maintaining the contact surfaces for a new connector half. This protector maintains sterility on the to-be-exposed surfaces and the conductor pathway is protected until the new member and protector are to be brought into mounted position. A manipulating movement to effect a penetration or piercing of the protector wall is needed to provide a fluid-flow pathway.

The embodiments of FIGS. 8 A through 10 D anticipate the use of a supply conduit having a hub with or without a piercing fitment such as the needle 130 shown mounted on a conventional syringe. A secured needle is shown in FIG. 8 A and a tapered reduced hub is shown as in FIGS. 9 A and 10 A. In FIGS. 8 A, B, C and 9 it is anticipated that the connector have a tapered recess leading the fluid flow toward the valve 106. Connector 188 has a hub projection and a taper that is contoured to mate and seat in a recess formed in the receiver and adapted to receive a connected length of tubing.

The embodiments as shown in the views of FIGS. 8 and 9 are very similar and provide for the fluid to be transferred from an initially stored condition in a supply conduit or a syringe. Syringe 86 has a needle and syringe 186 uses only the small hub end 104. When a needle 130 is used a piercing of the diaphragm 94 is made before fluid transfer. When syringe 186 is used and no needle is present a penetration of the resilient member is achieved when and as the small tapered end 104 opens the duckbill valve 106 such as by fluid pressure. The receiver 98 remains on connector half 88 or 188 during use and discarding of the syringe. The tubular sheath 90 may be rigid or semirigid to provide the desired guide means.

The flexible tubing 60 as shown in FIG. 3 may also be mounted on a short projecting portion 101 as in FIG. 8 C. In a like manner the tubing 28 of FIG. 2 may be mounted on a very similar projecting portion rather than be secured in a recess 26. Usually, the connector portions 20, 120, 22, 122, 220, 88, 188 and 98 are molded of a plastic which is acceptable to government regulatory agencies. Molding is suggested as the most inexpensive means for producing large quantities with acceptable tolerances and low cost commensurate with the accuracy and quality needed. Tubular sheath 90 or 190 is also made to suit the manufacturing conditions and syringe sizes. Sterility of the receiver and maintaining same is essential. This sterility is necessary for both dialysis and for blood pheresis procedures. The resilient material used in the diaphragm and for the protector of FIG. 2 and others is of material approved for the specific use by government agencies.

It is contemplated that the sterile connection device has a first and second substantially rigid connection half and within is a resilient protector member with a wall portion which is penetrated by a small rigid structure portion of the first connection half. This penetration may be by a needle in which instance the protector has a wall that is pierced by the needle, or without a needle the protector has a slit or duckbill valve that is responsive to the inserting action and/or fluid pressure provided by a small hub end such as on a syringe or the like. For example, rather than the needle of FIGS. 1 through 7 the female connection half 20, 120 or 220 is shown with a small hub or projecting end such as member 104 in FIGS. 9 A and 10 A. The resiliency of the protector member provides a residual bias that effects a closing of the slit or valve to provide the desired exclusion. The first connection half may be a molded portion or may be a syringe with or without a needle but with separation of the halves the protector member provides a barrier to unwanted contamination.

The protector exemplified in FIGS. 11 A and 11 B is rigid but has a one-way valve means utilizing a biased member to close a passageway. With the protector positioned on the extending tubular portion of the connector this effluent connector remains sterile during fluid transfer and separation. Reverse or return flow through this one-way valve means is not contemplated. It is to be noted that the connector in this device may be used for other than ambulatory dialysis.

The several means for retaining the connector halves in the desired assembly condition suggests that in many, if not all, of the devices that rotational movement of one half to the other is possible and probable. Although the size of illustration of the several components are enlarged for illustration, size and length is merely a matter of selection for the intended use.

Terms such as "left", "right", "up", "down", "bottom", "top", "front", "back", "in", "out" and the like are applicable to the embodiments shown and described in conjunction with the drawings. These terms are merely for the purposes of description and do not necessarily apply to the position in which the sterile connection device may be constructed or used.

While particular embodiments of the sterile connector apparatus have been shown and described it is to be understood that the invention is not limited thereto and protection is sought to the broadest extent the prior art allows.

What is claimed is:

1. A sterile connection device adapted for connecting a source of fluid from an influent connector to an effluent connector and providing a resilient protector member carried by the effluent connector, this protector member having an initially imperforate barrier wall and when the connectors are brought to a closed condition a sharpened hollow needle carried by the influent connector penetrates said resilient barrier wall to establish a fluid flow path and when the connectors are caused to be separated the penetration of the barrier wall by the hollow needle is discontinued with the needle remaining in the influent connector, this withdrawal of the needle allowing the residual bias in the protector to close the penetration site in the barrier wall and provide exclusion of unwanted contaminants into the discharge conduit, said sterile connector device including:

(a) an influent connector providing a female configuration with a cylindrically-formed interior in which at least the outer portion thereof is formed with a precise diameter tubular skirt portion and made as a stepped configuration with a smaller diameter portion extending forwardly of and from the skirt portion and with this differential in diameters forming and providing a stop shoulder, said connector having the opposite end a closing end in which a sharpened hollow needle is carried in and by a post portion of a given extent, said post portion extending into the cylindrically-formed interior and with the sharpened needle extending from said post portion a short distance into said tubular skirt portion with the remaining skirt portion open to the end and providing a smooth circular cavity;

(b) a protector member of resilient material having sufficient residual bias to close an aperture formed in a barrier wall portion of said protector member, said aperture formed by an inserted needle carried in and by the influent connector, said protector member having a forward and a rearward end and of generally circular configuration, the rearward portion being a skirt having an interior diameter of precise size and with this rearward portion integrally connected to said forward portion, the forwardly extending portion of the resilient protector member being formed as a reduced diameter portion of the rearward skirt portion, with this reduced diameter providing a free fit in the smaller diameter stepped bore in the influent connector, and between the forwardly extending portion and the rearwardly extending skirt portion of the resilient protector member is a differential of diameters which provides a stop shoulder adapted to engage the stop shoulder in the influent connector to establish the limit for said closed condition and position;

(c) a substantially rigid effluent connector providing a male configuration with a fluid pathway and conduit formed in a rear-end portion thereof and with said pathway and conduit substantially central of said connector, said connector having a tubular forwardly extending portion and a larger rearwardly extending enlarged tubular portion providing a shoulder at the joining of said external portions, this forwardly tubular portion sized to releaseably retain the outer skirt portion of the protector member and providing therewith a friction fit with the outer surface diameter of tubular forwardly-extending portion of the effluent connector, the rearwardly enlarged portion of the effluent connector sized to provide a mating and sliding fit within the tubular skirt portion of the influent connector, and (d) a forwardly-extending portion of the protector member sized to be a free sliding fit within the tubular skirt portion of the influent connector and forming in this forwardly-extending portion of the resilient protector member a central recess of a diameter to provide a free sliding fit on the post of the influent connector, said central recess of a depth sufficient to accept much of the post, with said extending portion of the resilient protector member and central recess therein providing means to prevent unwanted exposure to exterior contaminants, including fingers, when the influent connector and needle are removed, this recess terminating with said barrier wall which is of a thickness to be penetrated by the sharpened needle when the influent and effluent connectors are brought to closed condition.

2. A sterile connection device as in claim 1 in which the effluent connector has at least two pins extending outwardly and adapted to enter and be retained in L-shaped cutouts formed in said influent connector to effect selective connection and disconnection by a bayonet construction as provided on the influent and effluent halves.

3. A sterile connection device, as in claim 1, in which the resilient protector member at the barrier wall and opposite the central recess is formed with a rearwardly extending tubular portion whose outer diameter is sized to provide an internal guide and retaining means at and on the interior diameter portion of the forwardly extending portion of the effluent connector.

* * * * *